United States Patent
Vidlund et al.

(10) Patent No.: US 10,398,880 B2
(45) Date of Patent: Sep. 3, 2019

(54) MEDICAL SYSTEMS, DEVICES, AND RELATED METHODS

(71) Applicant: J.D. Franco & Co., LLC, Plano, TX (US)

(72) Inventors: Robert Vidlund, Forest Lake, MN (US); Michael Calhoun, Lighthouse Point, FL (US)

(73) Assignee: J.D. Franco & Co., LLC, Plano, TX (US)

(*) Notice: Subject to any disclaimer, the term of this patent is extended or adjusted under 35 U.S.C. 154(b) by 0 days.

(21) Appl. No.: 16/178,163

(22) Filed: Nov. 1, 2018

(65) Prior Publication Data

US 2019/0126013 A1   May 2, 2019

Related U.S. Application Data (60) Provisional application No. 62/580,665, filed on Nov. 2, 2017.

(51) Int. Cl.
| | |
|---|---|
| *A61M 25/10* | (2013.01) |
| *A61B 17/12* | (2006.01) |
| *A61M 25/06* | (2006.01) |
| *A61B 17/22* | (2006.01) |

(52) U.S. Cl.
CPC ... *A61M 25/1011* (2013.01); *A61B 17/12022* (2013.01); *A61M 25/104* (2013.01); *A61B 2017/22001* (2013.01); *A61B 2017/22067* (2013.01); *A61M 2025/0681* (2013.01)

(58) Field of Classification Search
CPC .............. A61B 17/12045; A61F 9/007; A61M 25/1011; A61M 2025/1097
See application file for complete search history.

(56) References Cited

U.S. PATENT DOCUMENTS

| | | |
|---|---|---|
| 2,690,595 A | 10/1954 | Raiche |
| 3,367,101 A | 2/1968 | Garnet et al. |
| 3,435,826 A | 4/1969 | Fogarty |
| (Continued) | | |

FOREIGN PATENT DOCUMENTS

| | | |
|---|---|---|
| WO | WO 98/52639 A1 | 11/1998 |
| WO | WO 98/53761 A1 | 12/1998 |
| (Continued) | | |

OTHER PUBLICATIONS

Altinbas, N.K. et al, "Effect of Carotid Artery Stenting on Ophthalmic Artery Flow Patterns," Journal of Ultrasound Medicine, 2014; 33: pp. 629-638.

(Continued)

*Primary Examiner* — Alexander J Orkin
(74) *Attorney, Agent, or Firm* — Bookoff McAndrews, PLLC (57) ABSTRACT

A method may include inflating a first balloon within an internal carotid artery so as to block antegrade flow of blood into an ophthalmic artery. Additionally, the method may include maintaining antegrade flow of blood in the internal carotid artery via a perfusion lumen in the first balloon. Further, the method may include inserting a device into the ophthalmic artery via a lumen extending through a portion of the first balloon to a side opening in the first balloon.

17 Claims, 7 Drawing Sheets

(56) References Cited

U.S. PATENT DOCUMENTS

| | | | |
|---|---|---|---|
| 4,224,929 A * | 9/1980 | Furihata | A61B 1/00082 600/107 |
| 4,403,612 A | 9/1983 | Fogarty | |
| 4,926,858 A | 5/1990 | Gifford, III et al. | |
| 5,000,734 A * | 3/1991 | Boussignac | A61M 25/10 604/103.06 |
| 5,026,384 A | 6/1991 | Farr et al. | |
| 5,176,693 A | 1/1993 | Pannek, Jr. | |
| 5,395,311 A | 3/1995 | Andrews | |
| 5,554,119 A * | 9/1996 | Harrison | A61M 25/1002 604/101.05 |
| 5,709,701 A | 1/1998 | Parodi | |
| 5,820,595 A | 10/1998 | Parodi | |
| 5,897,567 A | 4/1999 | Ressemann et al. | |
| 5,951,514 A * | 9/1999 | Sahota | A61F 2/958 604/101.05 |
| 6,146,370 A | 11/2000 | Barbut | |
| 6,206,868 B1 | 3/2001 | Parodi | |
| 6,302,908 B1 | 10/2001 | Parodi | |
| 6,336,933 B1 | 1/2002 | Parodi | |
| 6,344,054 B1 | 2/2002 | Parodi | |
| 6,413,235 B1 | 7/2002 | Parodi | |
| 6,423,032 B2 | 7/2002 | Parodi | |
| 6,540,712 B1 | 4/2003 | Parodi et al. | |
| 6,623,471 B1 | 9/2003 | Barbut | |
| 6,641,573 B1 | 11/2003 | Parodi | |
| 6,645,222 B1 | 11/2003 | Parodi et al. | |
| 6,824,558 B2 | 11/2004 | Parodi | |
| 6,827,726 B2 | 12/2004 | Parodi | |
| 6,837,881 B1 | 1/2005 | Barbut | |
| 6,855,162 B2 | 2/2005 | Parodi | |
| 6,902,540 B2 | 6/2005 | Dorros et al. | |
| 6,905,490 B2 | 6/2005 | Parodi | |
| 6,908,474 B2 | 6/2005 | Hogendijk et al. | |
| 6,929,634 B2 | 8/2005 | Dorros et al. | |
| 6,936,053 B1 | 8/2005 | Weiss | |
| 6,936,060 B2 | 8/2005 | Hogendijk et al. | |
| 7,214,201 B2 | 5/2007 | Burmeister et al. | |
| 7,235,095 B2 | 6/2007 | Haverkost et al. | |
| 7,309,334 B2 | 12/2007 | Von Hoffmann | |
| 7,384,411 B1 * | 6/2008 | Condado | A61M 25/0075 604/101.01 |
| 7,604,612 B2 | 10/2009 | Ressemann et al. | |
| 7,867,273 B2 | 1/2011 | Pappas et al. | |
| 7,901,445 B2 | 3/2011 | Walker et al. | |
| 7,927,347 B2 | 4/2011 | Hogendijk et al. | |
| 8,157,760 B2 | 4/2012 | Criado et al. | |
| 8,353,850 B2 | 1/2013 | Ressemann et al. | |
| 8,545,432 B2 | 10/2013 | Renati et al. | |
| 8,834,404 B2 | 9/2014 | Beaudin | |
| 8,852,226 B2 | 10/2014 | Gilson et al. | |
| 8,863,631 B1 | 10/2014 | Janardhan et al. | |
| 9,078,682 B2 | 7/2015 | Lenker et al. | |
| 9,241,699 B1 | 1/2016 | Kume et al. | |
| 9,259,215 B2 | 2/2016 | Chou et al. | |
| 9,265,512 B2 | 2/2016 | Garrison et al. | |
| 2001/0001114 A1 | 5/2001 | Tsugita et al. | |
| 2002/0087128 A1 | 7/2002 | Paques et al. | |
| 2002/0151922 A1 | 10/2002 | Hogendijk et al. | |
| 2002/0165573 A1 * | 11/2002 | Barbut | A61F 2/013 606/194 |
| 2003/0023200 A1 | 1/2003 | Barbut et al. | |
| 2003/0023227 A1 | 1/2003 | Zadno-Azizi et al. | |
| 2003/0199802 A1 | 10/2003 | Barbut | |
| 2003/0199819 A1 | 10/2003 | Beck | |
| 2003/0203958 A1 | 10/2003 | Kunz et al. | |
| 2005/0149117 A1 | 7/2005 | Khosravi et al. | |
| 2006/0136022 A1 | 6/2006 | Wong, Jr. et al. | |
| 2006/0259132 A1 | 11/2006 | Schaffer et al. | |
| 2008/0027519 A1 | 1/2008 | Guerrero | |
| 2008/0243229 A1 | 10/2008 | Wallace et al. | |
| 2009/0018455 A1 | 1/2009 | Chang | |
| 2009/0024072 A1 | 1/2009 | Criado et al. | |
| 2009/0030323 A1 | 1/2009 | Fawzi et al. | |
| 2010/0076365 A1 * | 3/2010 | Riina | A61B 17/12022 604/8 |
| 2010/0125244 A1 | 5/2010 | McAndrew | |
| 2011/0143993 A1 | 6/2011 | Langer et al. | |
| 2011/0152683 A1 | 6/2011 | Gerrans et al. | |
| 2011/0160762 A1 | 6/2011 | Hogendijk et al. | |
| 2012/0046679 A1 | 2/2012 | Patel et al. | |
| 2012/0078287 A1 | 3/2012 | Barbut | |
| 2012/0101510 A1 | 4/2012 | Lenker et al. | |
| 2013/0197621 A1 | 8/2013 | Ryan et al. | |
| 2013/0281788 A1 | 10/2013 | Garrison | |
| 2014/0154246 A1 | 6/2014 | Robinson et al. | |
| 2015/0272732 A1 * | 10/2015 | Tilson | A61M 25/1002 623/2.11 |
| 2015/0313607 A1 | 11/2015 | Zhadkevich | |
| 2015/0366580 A1 | 12/2015 | Lenihan et al. | |
| 2016/0166754 A1 | 6/2016 | Kassab et al. | |
| 2017/0164963 A1 * | 6/2017 | Goyal | A61B 17/22 |

FOREIGN PATENT DOCUMENTS

| | | | |
|---|---|---|---|
| WO | WO 00/54673 A1 | 9/2000 | |
| WO | WO 03/018085 A2 | 3/2003 | |
| WO | WO 2007/103464 A2 | 9/2007 | |
| WO | WO 2014/022866 A1 | 2/2014 | |
| WO | WO 2016/109586 A1 | 7/2016 | |
| WO | WO 2017/156333 A1 | 9/2017 | |

OTHER PUBLICATIONS

Ambarki, K. et al., "Blood Flow of Ophthalmic Artery in Healthy Individuals Determined by Phase-Contrast Magnetic Resonance Imaging," Investigative Ophthalmology & Visual Science, 2013; 54: pp. 2738-2745.

Hayreh, S.S., "The Ophthalmic Artery III. Branches," British Journal of Ophthalmology, 1962, 46, pp. 212-247.

Hwang, G. et al., "Reversal of Ischemic Retinopathy Following Balloon Angioplasty of a Stenotic Ophthalmic Artery." Journal of Neuro-Ophthalmology 30.3, 2010, pp. 228-230.

Kane, A.G. et al., "Reduced Caliber of the Internal Carotid Artery: A Normal Finding with Ipsilateral Absence or Hypoplasia of the A1 Segment," American Journal of Neuroradiology, 1996; 17: pp. 1295-1301.

Kawa, M.P. et al., "Complement System in Pathogenesis of AMD: Dual Player in Degeneration and Protection of Retinal Tissue," Hindawi Publishing Corporation, Journal of Immunology Research, vol. 2014, Article ID 483960, 12 pages.

Klein, R. et al., "Vasodilators, Blood Pressure-Lowering Medications, and Age-Related Macular Degeneration," American Academy of Ophthalmology, 2014, vol. 121, Issue 8, pp. 1604-1611.

Kooragayala, K. et al., "Quanitification of Oxygen Consumption in Retina Ex Vivo Demonstrates Limited Reserve Capacity of Photoreceptor Mitochondria," Investigative Ophthalmology & Visual Science, 2015; 56: pp. 8428-8436.

Krejza, J. et al., "Carotid Artery Diameter in Men and Women and the Relation to Body and Neck Size," Stroke, 2006; 3 pages.

Lanzino, G. et al., "Treatment of Carotid Artery Stenosis: Medical Therapy, Surgery, or Stenting?," Mayo Clinic Proceedings, Apr. 2009; 84(4), pp. 362-368.

Michalinos, A. et al., "Anatomy of the Ophthalmic Artery: A Review concerning Its Modern Surgical and Clinical Applications," Hindawi Publishing Corporation, Anatomy Research International, vol. 2015, Article ID 591961, 8 pages.

Paques, M. et al., "Superselective ophthalmic artery fibrinolytic therapy for the treatment of central retinal vein occlusion." British Journal of Ophthalmology, 2000, 84: 1387-1391.

Tan, P.L. et al., "AMD and the alternative complement pathway: genetics and functional implications," Human Genomics, 2016, 10:23, 13 pages.

Xu, H. et al., "Targeting the complement system for the management of retinal inflammatory and degenerative diseases," European Journal of Pharmacology, 2016, 787, pp. 94-104.

Yamane, T. et al., "The technique of ophthalmic arterial infusion therapy for patients with intraocular retinoblastoma," International (56) References Cited

OTHER PUBLICATIONS

Journal of Clinical Oncology, Apr. 2004; vol. 9, Issue 2, pp. 69-73.
Zeumer, H. et al., "Local intra-arterial fibrinolytic therapy in patients with stroke: urokinase versus recombinant tissue plagminogen activator (r-TPA)," Neuroradiology, 1993; 35: pp. 159-162.
Zipfel, P.F., et al., "The Role of Complement in AMD," Inflammation and Retinal Disease: Complement Biology and Pathology, Advances in Experimental Medicine and Biology, 2010, 703, pp. 9-24.
Examination Report No. 2 for AU Application No. 2013296195, dated Jun. 27, 2017 (6 pages).
Notice of Allowance for KR 20157005602, dated Sep. 25, 2017 (3 pages).
Loh, K. et al., "Prevention and management of vision loss relating to facial filler injections." Singapore Medical Journal, 2016; 57(8): 438-443.
International Search Report and Written Opinion for International Application No. PCT/US2017/0051551, dated Dec. 15, 2017 (14 pages).
International Search Report and Written Opinion for International Application No. PCT/US2017/0052901, dated Dec. 8, 2017 (9 pages).

\* cited by examiner

MEDICAL SYSTEMS, DEVICES, AND RELATED METHODS

CROSS-REFERENCE TO RELATED APPLICATIONS

This patent application claims the benefit of priority under 35 U.S.C. § 119 to U.S. Provisional Patent Application No. 62/580,665, filed Nov. 2, 2017, which is herein incorporated by reference in its entirety.

TECHNICAL FIELD

Various aspects of the present disclosure relate generally to medical systems, devices, and related methods. More specifically, the present disclosure relates to medical systems and/or devices for achieving reverse blood flow.

BACKGROUND

Vasculature of a subject (also referred to as patient) may occasionally become stenosed, occluded, partially occluded, blocked, narrowed, or otherwise compromised such that transfer of blood through the vasculature is impeded, lessened, and/or prevented. That is, the blood carrying capacity of such a compromised vessel is reduced or otherwise insufficient. The vasculature may become occluded, stenosed, or at least partially blocked due to the deposit of plaque, emboli, or other such material on the walls of the vasculature. To avoid serious and/or permanent injury, one or more medical procedures or interventions may be performed. Such procedures may include, for example, angioplasty, atherectomy, stenting, or the like in which a constricted, narrowed, occluded, or otherwise partially blocked region of the vasculature is opened, widened, or unblocked so as to allow or maintain blood flow therethrough. Often, however, such procedures may loosen and/or fragment plaque, emboli, or other such material. The fragmented plaque, emboli, or other material may travel downstream with a flow of blood passing through the vasculature and potentially result in a stroke or other embolic event.

The systems, devices, and methods of the current disclosure may rectify some of the deficiencies described above or address other aspects of the prior art.

SUMMARY

Examples of the present disclosure relate to, among other things, medical devices and procedures. Each of the examples disclosed herein may include one or more of the features described in connection with any of the other disclosed examples.

In one example, a method may include inflating a first balloon within an internal carotid artery so as to block antegrade flow of blood through the internal carotid artery. Additionally, the method may include deploying a second balloon within the internal carotid artery distal of the first balloon and increasing a flow rate of blood passing the second balloon via expansion of the second balloon. Further, the method may include maintaining antegrade flow of blood between a common carotid artery and an external carotid artery of a subject.

Examples of the method may include one or more of the following features. The method may include adjusting a degree of expansion of the second balloon. Deploying the second balloon may include positioning at least a portion of the second balloon distally of an ophthalmic artery of a subject. The method may include inducing retrograde blood flow in an ophthalmic artery of the subject.

In a further aspect, a method may include inflating a first balloon within an internal carotid artery of the subject proximal of an ophthalmic artery of a subject. Additionally, the method may include inflating a second balloon within the internal carotid artery distal of the ophthalmic artery, and inducing retrograde blood flow in the ophthalmic artery. Further, the method may include maintaining antegrade flow of blood between a common carotid artery and an external carotid artery of a subject.

Examples of the method may include passing the induced retrograde blood flow through a channel of the first balloon.

In a further aspect, a method may include inflating a first balloon within an internal carotid artery so as to block antegrade flow of blood into an ophthalmic artery. Further, the method may include maintaining antegrade flow of blood in the internal carotid artery via a perfusion lumen in the first balloon. Additionally, the method may include inserting a device into the ophthalmic artery via a lumen extending through a portion of the first balloon to a side opening in the first balloon.

Examples of the method may include one or more of the following features. The method may further include inflating a second balloon distally of the ophthalmic artery. Additionally, the method may include inducing retrograde blood flow in the ophthalmic artery of the subject. Also, inflating the first balloon may form a seal against a wall of the internal carotid artery.

In an additional aspect, a method may include inflating a first balloon within an internal carotid artery of a subject proximal of an ophthalmic artery of the subject. Further, the method may include inflating a second balloon within the internal carotid artery distal of the ophthalmic artery. Also, the method may include stopping antegrade blood flow in the ophthalmic artery, and maintaining antegrade blood flow in the internal carotid artery of the subject.

Examples of the method may include on or more of the following features. The method may include inducing retrograde blood flow in the ophthalmic artery. Additionally, the method may include passing the induced retrograde blood flow through a channel of the first balloon. Also, the method may include inserting a device into the ophthalmic artery via a lumen extending through a portion of the first balloon to a side opening in the first balloon.

In a further aspect, a method may include positioning a balloon within an internal carotid artery. The balloon may include an opening extending through a side wall of the balloon. The method also may include expanding the balloon so as to contact a wall of the internal carotid artery and aligning the opening of the balloon with an ophthalmic artery. Additionally, the expanding the balloon may include adjusting a blood flow rate of the ophthalmic artery.

Examples of the method may further include one or more of the following features. The method may include permitting blood flow through the opening of the balloon. Permitting blood flow through the opening may include permitting induced retrograde blood from the ophthalmic artery, through the opening, to a location proximal of the balloon. Further, the method may include fluidly coupling a region of the internal carotid artery proximal of the balloon with a region of the internal carotid artery distal of the balloon via a lumen disparate from the side wall opening of the balloon.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not necessarily include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value unless otherwise stated.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical systems, devices, and methods for treating internal areas of a patient's body by establishing reverse blood flow in the ophthalmic artery.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to a medical professional using the medical device or insertion device. In contrast, "distal" refers to a position relatively further away from the medical professional using the medical device or insertion device, or closer to the interior of the body.

The terms "downstream" or "antegrade" and "upstream" or "retrograde," when used herein in relation to the subject's vasculature, refer respectively, to the direction of blood flow and the direction opposite that of blood flow, respectively. In the arterial system, "downstream" or "antegrade" refers to the direction further from the heart, while "upstream" or "retrograde" refers to the direction closer to the heart.

"Reverse flow," as used herein, is the flow of blood opposite to the direction of blood flow under normal blood flow conditions. In this disclosure, "reverse flow" and "retrograde flow" are used synonymously. Reverse flow may be achieved by creating a pressure gradient so blood flow is reversed and directed, for example, from the treatment site into a lumen of a medical device to be rerouted to another location.

Figure 1:
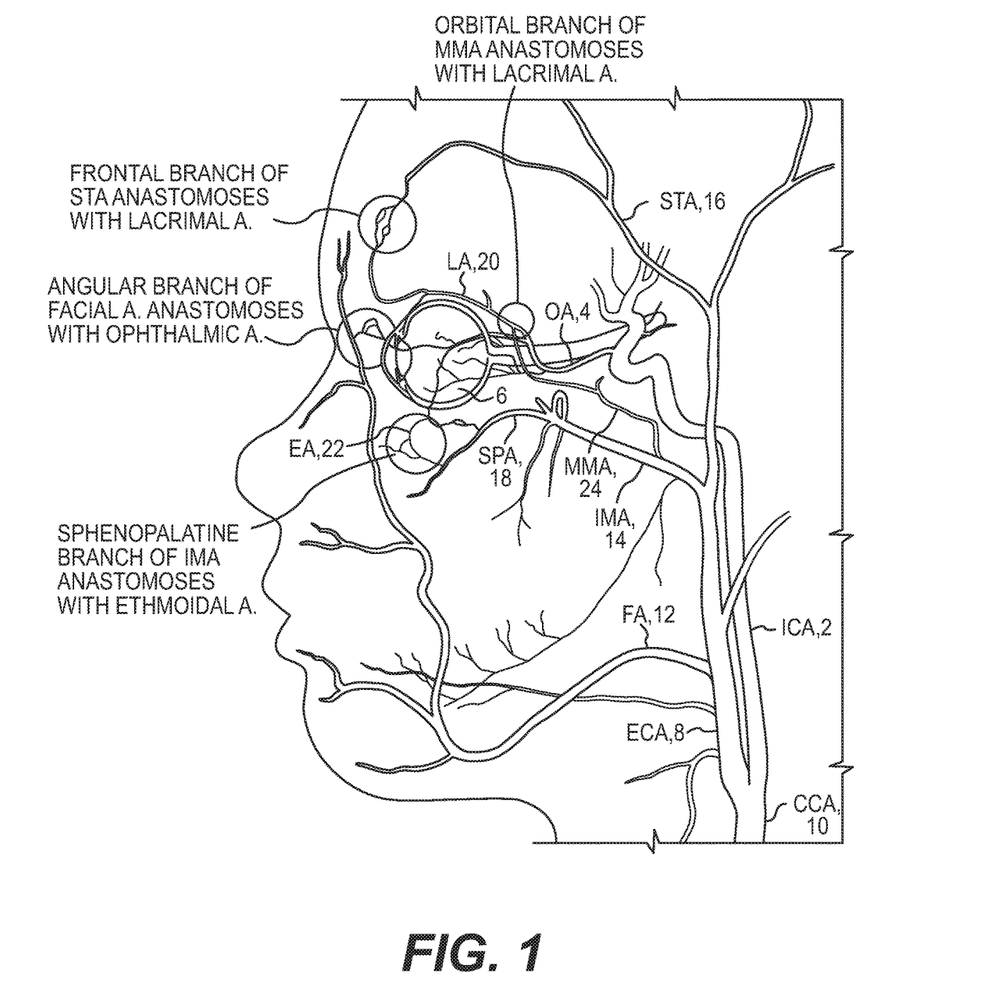
FIG. 1 illustrates vasculature relating to an ophthalmic artery (OA) of a subject.

FIG. 1 illustrates various vasculature structures a subject. For example, blood may flow from the heart through the internal carotid artery (ICA) 2 to the ophthalmic artery (OA) 4 to an eye 6 of the subject. Additionally, the external carotid artery (ECA) 8 may supply a flow of blood to the face and neck of a subject. Each of the ICA 2 and ECA 8 branches off of the common carotid artery (CCA) 10 of the subject. The ECA 8, in turn, branches into the facial artery (FA) 12, the internal maxillary artery (IMA) 14, and the supra trochlear artery (STA) 16. IMA 14 then branches into the sphenopalatine artery (SPA) 18, and the middle meningeal artery (MMA) 24. OA 4 includes a number of branches such as the lacrimal artery (LA) 20 and the ethmoidal artery (EA) 22. ICA 2 and ECA 8 have several anastomoses (e.g., connections or junctures) which permit the exchange of blood therebetween. Specifically, the anastomoses that relate to OA 4 include: (1) anastomosis between SPA 18 and EA 22; (2) anastomosis between MMA 24 and LA 20; (3) anastomosis between STA 16 and LA 20; and (4) anastomosis between FA 12 and OA 4.

Figure 2A:
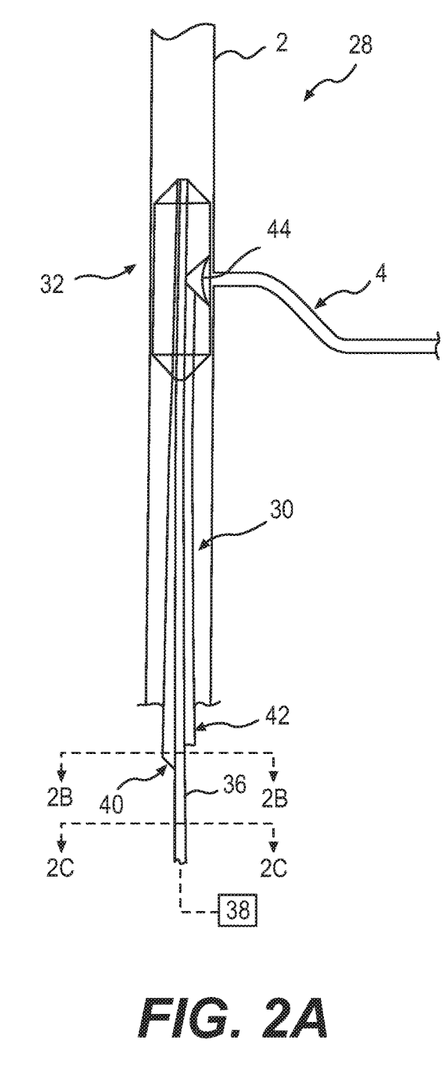
FIG. 2A illustrates an exemplary system for establishing reverse flow in the OA.

Currently, a number of techniques have been developed for the occlusion of one or both of the ECA 8 or the CCA 10. Such procedures cannot, however, ensure the induction of retrograde blood flow in OA 4. FIG. 2A illustrates an exemplary system 28 for establishing reverse flow in OA 4. As shown in FIG. 2A, such a system may include a sheath 30 and an inflatable balloon 32. Balloon 32 may be mounted on or positioned about an external surface of sheath 30. In some arrangements, balloon 32 may be formed as a cuff encircling a portion (e.g., a distal end portion) of sheath 30. Balloon 32 may be a compliant balloon and constructed of any appropriate materials (e.g., urethane polymer or thermoplastic rubber elastomer). Balloon 32 may have any appropriate shape and size. For example, upon expansion of balloon 32, a cross-sectional dimension (e.g., diameter) of balloon 32 may be sized so as to contact a wall of ICA 2. That is, a cross-sectional dimension (e.g., diameter) of balloon 32 in an expanded state may average about 4.62 mm.

Sheath 30 (e.g., a catheter) may include a plurality of lumens. For example, a first lumen 36 may be a balloon inflation lumen. That is, first lumen 36 may have a first end fluidly coupled with a source of inflation fluid 38 (e.g., a gas such as air, or a liquid such as water or saline). A second end of first lumen 36 may extend through balloon 32. Additionally, first lumen 36 may be fluidly coupled to an interior of balloon 32 via a side port/valve (not shown) such that upon delivery of fluid from source 38 to balloon 32, balloon 32 may expand from a first, uninflated configuration (not shown) to an expanded configuration as shown in FIG. 2A. Additionally, first lumen 36 may be coupled to a source (not shown) of negative pressure (e.g., vacuum) such that upon actuation of the negative pressure source, balloon 32 may be deflated.

Figure 2B:
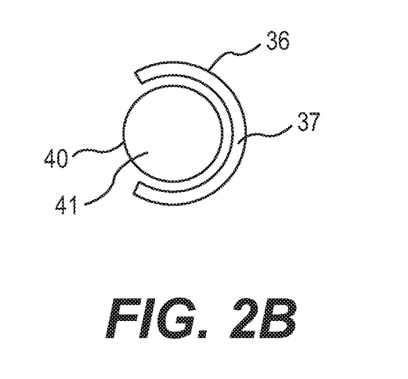
FIG. 2B illustrates a cross-sectional view of a portion of a sheath of the exemplary system of FIG. 2A, according to a first arrangement.
Figure 2C:
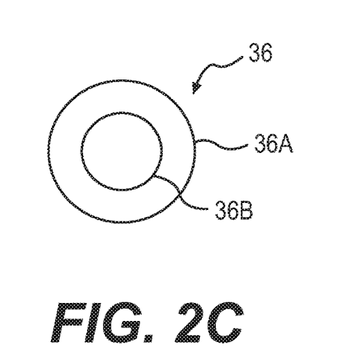
FIG. 2C illustrates a cross-sectional view of a portion of a sheath of the exemplary system of FIG. 2A, according to a further arrangement.

A second lumen 40 may extend through sheath 30 and between a proximal end and a distal end of sheath 30, e.g., distal to balloon 32. Second lumen 40 may be a guide lumen such that sheath 30 and balloon 32 may be delivered over a guidewire or the like via second lumen 40. As shown, second lumen 40 may be configured for "rapid exchange" (RE)

delivery. For example, as shown in FIG. 2B, second lumen 40 may include a generally circular cross-sectional shape, while first lumen 36 may include a generally semi-circular, crescent, or c-shaped cross-sectional shape along the entirety of its length. That is, as shown in FIG. 2B, second lumen 40 may be nested or otherwise received within an opening or space defined by first lumen 36. As such, a combined cross-sectional space or area occupied by first lumen 36 and second lumen 40 may be reduced. In such a manner, inflation fluid from source 38 may be passed through a c-shaped passage 37 within first lumen 36, while a guidewire or the like may be passed through a passage 41 of second lumen 40. Alternatively, second lumen 40 may be omitted and the system 28 may be arranged for "over-the-wire" (OTW) delivery. To that end, first lumen 36 may be dual-walled such that first lumen 36 includes an outer lumen wall 36A and an inner lumen wall 36B, as shown in FIG. 2C. In such an arrangement, inner lumen wall 36B may extend through balloon 32 such that system 28 may be advanced over a guidewire (not shown) via a lumen formed radially within inner lumen wall 36B. Additionally, outer lumen wall 36A may terminate at a proximal end of balloon 32. In such a manner, a space between outer lumen wall 36A and inner lumen wall 36B may be configured to deliver inflation fluid from source 28 to balloon 32.

A third lumen 42 may extend from a proximal end to an opening 44. Opening 44 may extend through a sidewall of balloon 32. That is, opening 44 enables communication between an environment (e.g., vasculature) within which balloon 32 is positioned and a proximal end of third lumen 42 (or sheath 30). As shown in FIG. 2A, at least a portion (e.g., a distal portion) of balloon 32 may be positioned distal to opening 44 while at least another portion (e.g., a proximal portion) of balloon 32 may be positioned proximal to opening 44.

In use, a medical professional may access ICA 2 via any appropriate manner (e.g., an arterial cut down, etc.). Additionally, the medical professional may position a guidewire within the vasculature of a subject, extending an end of the guidewire into ICA 2 to a position distal of a junction between CCA 10 and ECA 8, and optionally, distal to a junction between ICA 2 and OA 4. Once so positioned, sheath 30 may be advanced over the guidewire into position within ICA 2. For example, second lumen 40 of sheath 30 may be advanced over the guidewire until opening 44 of balloon 32 is aligned or otherwise across from OA 4. That is, sheath 30 may be advanced such that the distal portion of balloon 32 is positioned distal to OA 4 while a proximal portion of balloon 32 is positioned proximal of OA 4. Radiopaque or other markers may be placed just distal and just proximal to opening 44, and with suitable imaging or other viewing techniques, may assist in longitudinal and rotational positioning of sheath 32 and balloon 32. Once sheath 30 is positioned, the guidewire may be removed from second lumen 40 of sheath 30. Alternatively, the guidewire may remain within second lumen 40 during a remainder of the procedure.

Next, balloon 32 may be expanded. That is, source 38, coupled to first lumen 36, may be actuated so as to inflate balloon 32. Upon expansion of balloon 32, balloon 32 may contact a wall of ICA 2. Upon expansion, antegrade blood flow through ICA 2 may be prevented or blocked. However, as balloon 32 is positioned distal of the junction between CCA 10 and ECA 8, antegrade blood flow between CCA 10 and ECA 8 is maintained. Such a continuation of antegrade flow between CCA 10 and ECA 8 serves to supply the two most common OA 4 to ECA 8 anastomoses including anastomosis between SPA 18 and EA 22, and anastomosis between MMA 24 and LA 20 (FIG. 1). The antegrade flow of blood from CCA 10 and ECA 8 is maintained in order to ensure that an adequate supply of blood is available via the common anastomoses such that continuous retrograde movement of blood is ensured from OA 4 to ICA 2. These common anastomoses include the orbital branch of the middle meningeal artery (MMA) 24, the frontal branch of the supratrochlear artery (STA) 16, the angular branch of the facial artery (FA) 12, and the sphenopalatine branch of the internal maxillary artery (IMA) 14. While all of these anastomoses may not be present in every patient, enough of them are typically present to offer the potential pathway for feeding the ICA 2 with a blood supply to ensure continuous retrograde flow during reverse flow procedures. As such, any plaque, emboli, or other material dislodged and/or fragmented may be prevented from flowing from ICA 2 toward the eye 6 via OA 4, thereby preventing an embolic event (e.g., blindness, stroke, etc.). Alternatively, an additional balloon (not shown) may be inserted and inflated within the ECA 8 at a location distal of the junction between the ECA 8 and IMA 14. The retrograde flow of blood from OA 4 to ICA 2 may be passed through opening 44 and into third lumen 42 of sheath 30. Additionally, a proximal end of third lumen 42 may be coupled to a filter and a return line (not shown) to return the filtered retrograde blood flow into a venous return site (e.g., into the internal jugular vein (IJV) of the subject) via any appropriate manner.

Optionally, an additional device may be advanced through third lumen 42 and into OA 4. For example, a guidewire may be advanced through third lumen 42 into OA 4 such that one or more additional devices (e.g., balloons, stents, etc.) may be advanced into OA 4 for one or more additional procedures.

Figure 3:
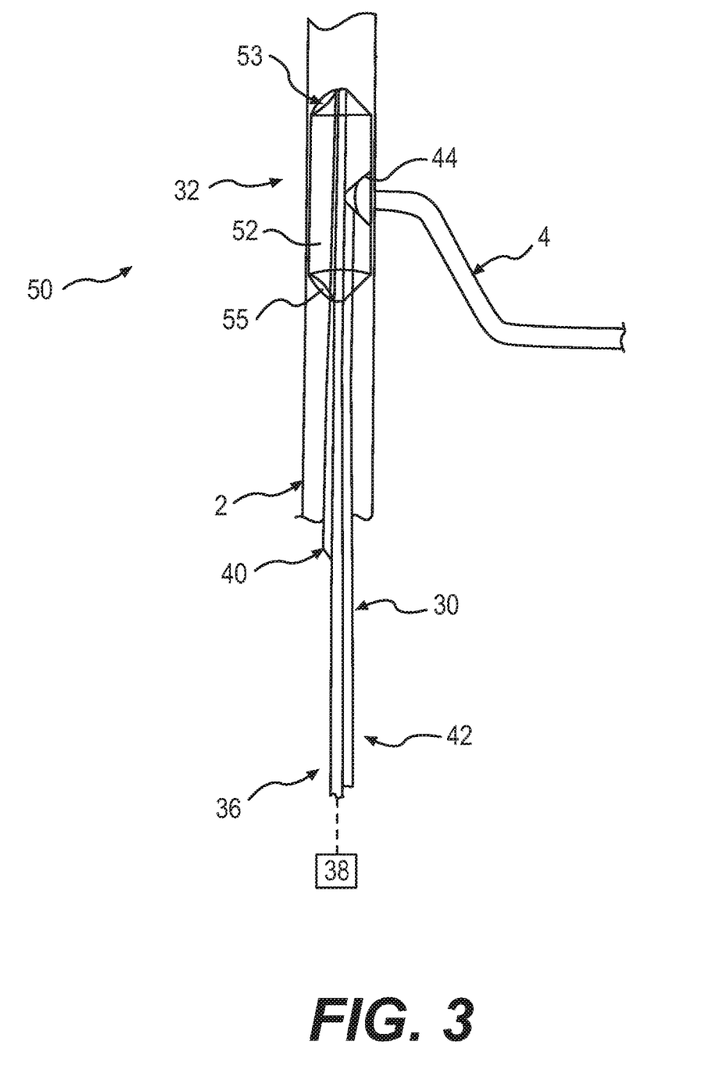
FIG. 3 illustrates a further exemplary system for establishing reverse flow in the OA.

FIG. 3 illustrates a further exemplary system 50 for establishing reverse flow in OA 4. The system 50 of FIG. 3 includes features similar to those of the system 28 of FIG. 2A, and like components are illustrated with the same numbers. For example, the system 50 of FIG. 3 includes sheath 30, a balloon 32, a first lumen 36 coupled to a source of inflation fluid 38, a second lumen 40, and a third lumen 42 terminating in an opening 44. In addition, the system 50 of FIG. 3 includes a fourth lumen 52. As shown, fourth lumen 52 extends through the length of balloon 32 so as to enable fluid communication between a region of ICA 2 proximal or upstream of balloon 32 and a region of ICA 2 distal or downstream of balloon 32, via openings 53 and 55 of fourth lumen 52. In some arrangements, fourth lumen 52 may enable retrograde ICA 2 blood flow to pass therethrough. Alternatively, fourth lumen 52 may comprise a perfusion lumen, thereby enabling antegrade blood flow through ICA 2. In this example, only the ICA 2 is blocked with a balloon. The ECA 8 and the CCA 10 will not have balloons placed in their respective lumens. When the ICA 2 is blocked to induce reverse flow, blood will flow out of the related segment of the ICA 2 and the OA 4 creating a lower blood pressure in the OA 4 and related anastomoses. This lower pressure will facilitate blood flow from a higher-pressure area (e.g., ECA 8). The overall blood flow circuit is enabled by allowing normal antegrade blood to flow up the CCA 10 and into the ECA 8. From the ECA 8, the previously described anastomoses provide a pathway for the blood to enter into the ICA 2. Blood will flow from the higher pressure ECA 8, through the anastomoses, into the OA 4 and out into the ICA 2 (e.g., in a retrograde fashion). From the ICA 2, the blood may be passed through a filter (not shown) and returned into the venous system. This method may preserve the normal antegrade flow of the ECA 8 while allowing for retrograde flow in the desired area of the OA 4 and ICA 2. While fourth lumen 52 is shown as a through lumen extending through balloon 32, in some arrangements, fourth lumen 52 (or a pair or plurality of fourth lumens 52) may be arranged as a channel(s) (e.g., a groove, indent or the like) extending along an outermost surface balloon 32. When balloon 32 is inflated, the channel is spaced between a surface of the balloon and the wall of ICA 2, such that blood may flow through the channel between points proximal and distal of balloon 32.

Figure 4:
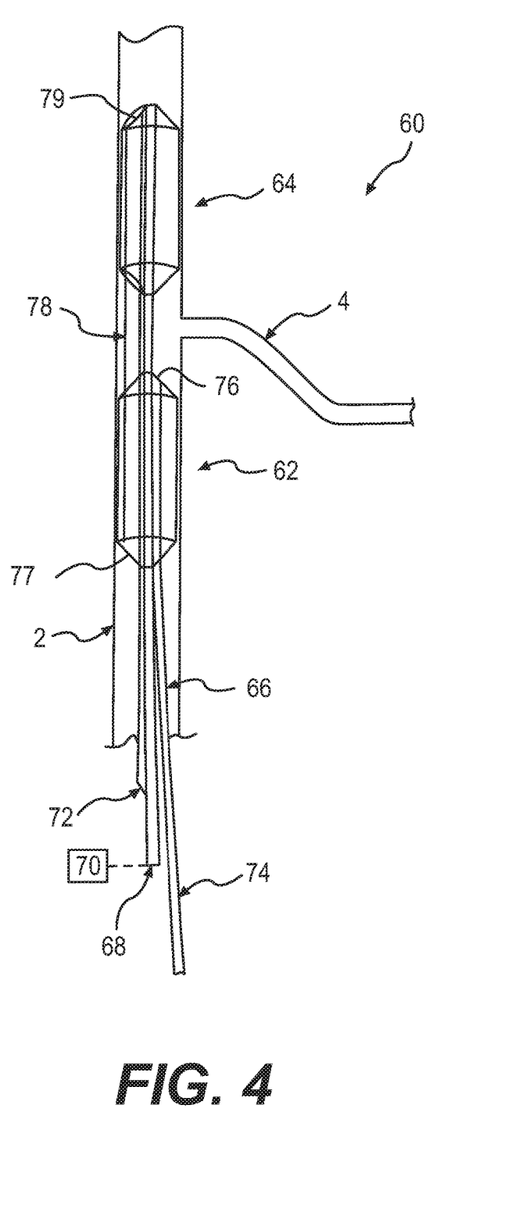
FIG. 4 illustrates another exemplary system for establishing reverse flow in the OA.

FIG. 4 illustrates a further exemplary system 60 for establishing reverse flow in OA 4. The system 60 of FIG. 4 includes features similar to those of the systems 28 and 50 of FIGS. 2A and 3, respectively, and like components are illustrated with the same reference numbers. In contrast to systems 28 and 50, however, system 60 includes a pair of balloons. For example, system 60 includes a first balloon 62 and a second balloon 64 coupled to a sheath 66. A first lumen 68, e.g., a balloon inflation lumen, may extend through sheath 66. First lumen 68 may have a first end fluidly coupled with a source of inflation fluid 70 (e.g., a gas such as air, or a liquid such as water or saline). A second end of first lumen 68 may extend through first balloon 62 and second balloon 64, and, via any appropriate arrangement of valve(s) or the like (not shown), be fluidly coupled to an interior of one or both of first balloon 62 and second balloon 64. Upon delivery of fluid from source 70 to balloon(s) 62, 64, balloon(s) 62, 64 may expand from a first, uninflated configuration (not shown) to a second, expanded configuration as shown in FIG. 4. That is, in some arrangements, a single lumen, e.g., first lumen 68, may simultaneously expand both the first balloon 62 and the second balloon 64. In a further arrangement, first lumen 68 may comprise a pair of lumens such that one of the pair of first lumens 68 may terminate within the interior of first balloon 62 while another of the pair of first lumens 68 terminates within the interior of second balloon 64. In such a manner, each of first balloon 62 and second balloon 64 may be individually expanded (e.g., inflated) and/or deflated.

Additionally, sheath 66 may include a second lumen 72, extending from a proximal end of sheath 66 to a distalmost end of sheath 66. Second lumen 72 may be a guide lumen such that sheath 66, first balloon 62, and second balloon 64 may be delivered over a guidewire or the like via second lumen 72. Second lumen 72 may be arranged as an "over-the-wire" (OTW) lumen or configured for "rapid exchange" (RE) delivery.

A third lumen 74 may extend from a proximal end to an opening 76 extending through a distal end portion of first balloon 62. Opening 76 enables communication between an environment (e.g., vasculature) within which first balloon 62 is positioned and a proximal end of third lumen 74 (or sheath 66). Notably, third lumen 74 terminates at opening 76 of first balloon 62, and does not extend through second balloon 64. A fourth lumen 78, however, extends along sheath 66 and through the length of first balloon 62 and second balloon 64, between proximal opening 77 and distal opening 79, so as to enable fluid communication between a region of ICA 2 proximal or upstream of first balloon 62 and a region of ICA 2 distal or downstream of second balloon 64. In some arrangements, fourth lumen 78 may enable retrograde blood flow to pass therethrough. Alternatively, fourth lumen 78 may comprise a perfusion lumen, thereby enabling antegrade blood flow through ICA 2. While fourth lumen 78 is shown as a through lumen extending through first balloon 62 and second balloon 64, in some arrangements, fourth lumen 78 (or a pair or plurality of fourth lumens 78) may be arranged as a channel(s) (e.g., a groove, indent or the like) extending along an outermost surface first balloon 62 and second balloon 64, similar to that discussed in connection with FIG. 3.

After accessing ICA 2 via any appropriate manner, the medical professional may position a guidewire within the vasculature of a subject, extending an end of the guidewire into ICA 2 to a position distal of a junction between CCA 10 and ECA 8, and optionally, distal to a junction between ICA 2 and OA 4. Once so positioned, sheath 66 may be advanced over the guidewire into position within ICA 2 such that second balloon 64 is positioned distal to OA 4 while a first balloon 62 is positioned proximal of OA 4. Once so positioned, the guidewire may be removed from second lumen 72 of sheath 66. Optionally, the guidewire may be left in second lumen 72 throughout the procedure.

Next, first balloon 62 and second balloon 64 may be expanded. That is, source 70, coupled to first lumen 68 (or pair of first lumens 68), may be actuated so as to inflate first balloon 62 and second balloon 64 (e.g., either simultaneously or individually). First balloon 62 may be expanded so as to contact a wall of ICA 2 upstream or proximal of OA 4, while second balloon 64 may be expanded so as to contact a wall of ICA 2 downstream or distal of OA 4. As first balloon 62 and second balloon 64 are both positioned distal of the junction between CCA 10 and ECA 8, antegrade blood flow between CCA 10 and ECA 8 is maintained. However, inflation or expansion of one or both of first balloon 62 and second balloon 64 induces a pressure differential in the vasculature such that retrograde blood flow is induced from OA 4 towards ICA 2. The induced retrograde blood flow may be passed through first balloon 62 and through sheath 66 via third lumen 74. As such, any plaque, emboli, or other material dislodged and/or fragmented may be prevented from flowing from ICA 2 toward the eye 6 via OA 4, thereby preventing an embolic event (e.g., blindness, stroke, etc.). A proximal end of third lumen 74 may be coupled to a filter and a return line (not shown) to return the filtered retrograde blood flow into a venous return site (e.g., into the internal jugular vein (IJV) of the subject) via any appropriate manner. Optionally, an additional device (e.g., one or more of a guidewire, a balloon, a stent, etc.) may be advanced through third lumen 74 and into OA 4 for one or more additional procedures, if deemed necessary or desirable by a medical professional. Further, fourth lumen 78, or a pair of fourth lumens 78, may enable antegrade ICA 2 and/or retrograde ICA 2 blood flow therethrough.

Figure 5:
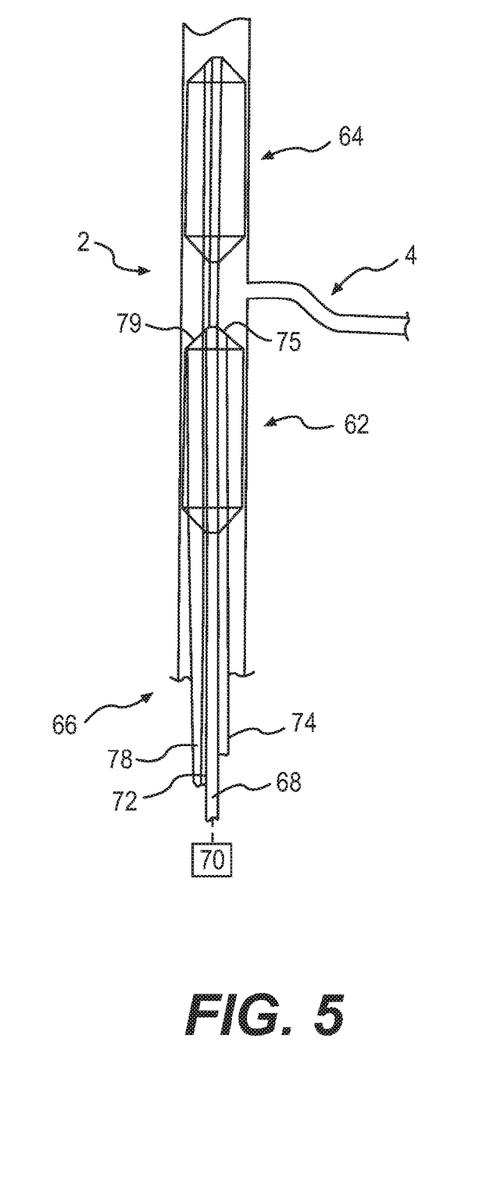
FIG. 5 illustrates a further exemplary system for establishing reverse flow in the OA.

Alternatively, as shown in FIG. 5, fourth lumen 78 may extend through only first balloon 62. That is, in contrast to the arrangement shown in FIG. 4 in which fourth lumen 78 extends through sheath 66, through first balloon 62, and through second balloon 64, fourth lumen 78 shown in FIG. 5 extends only through sheath 66 and through first balloon 62 and terminate in a distal opening 79. In such a manner, fourth lumen 78 may be used to convey retrograde blood flow from OA 4. That is, the retrograde flow of blood from OA 4 to ICA 2 may be passed through into fourth lumen 78 via distal opening 79. A proximal end of fourth lumen 78 may be coupled to a filter and a return line (not shown) to return the filtered retrograde blood flow into a venous return site (e.g., into the internal jugular vein (IJV) of the subject) via any appropriate manner. Since retrograde flow is enabled to exit via fourth lumen 78, third lumen 74 may be reserved for advancement and retraction of additional devices (e.g., one or more of a guidewire, a balloon, a stent, etc.) therethrough, out of a distal opening 75, and into OA 4 for one or more additional procedures, if deemed necessary or desirable by a medical professional.

Figure 6:
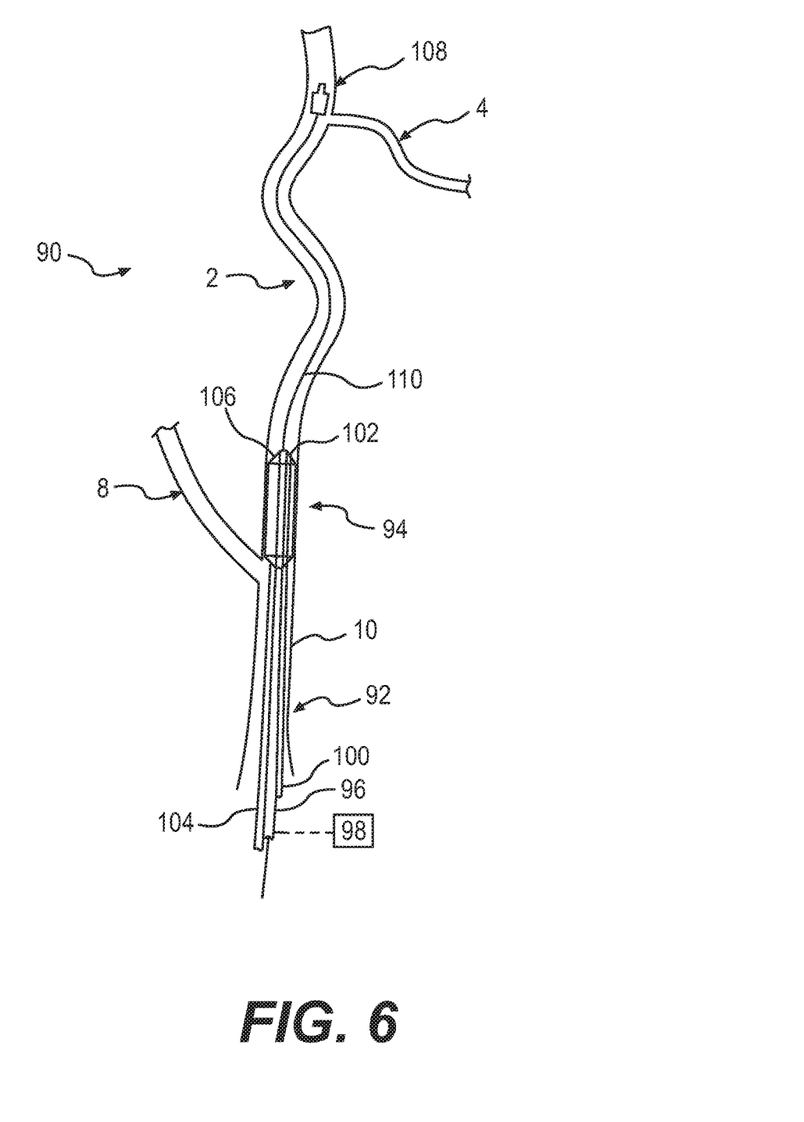
FIG. 6 illustrates another exemplary system for establishing reverse flow in the OA.

FIG. 6 illustrates a further exemplary system 90 for establishing reverse flow in OA 4. The system 90 may include a sheath 92 and a first (e.g., proximal) balloon 94. Sheath 90 (e.g., a catheter) may include a plurality of lumens. For example, a first lumen 96 may be a balloon inflation lumen. That is, first lumen 96 may have a first end fluidly coupled with a source of inflation fluid 98 (e.g., a gas such as air, or a liquid such as water or saline). A second end of first lumen 96 may extend through a distalmost end of first balloon 94. Additionally, first lumen 96 may be fluidly coupled to an interior of a first balloon 94 via a side port/valve (not shown). Upon delivery of fluid from source 98 to first balloon 94 via first lumen 96, first balloon 94 may expand from a first, uninflated configuration (not shown) to an expanded configuration as shown in FIG. 6. Additionally, first lumen 96 may be coupled to a source of negative pressure (e.g., vacuum) such that upon actuation of the negative pressure source, balloon 32 may be deflated. First lumen 96 also may facilitate delivery of sheath 92 and first balloon 94 to a desired location within the vasculature of a subject. In some arrangements, first lumen 96 may be arranged as an "over-the-wire" (OTW) lumen in which a guidewire may be thread through first lumen 96, from a proximal end to a distal end of first lumen 96. In other arrangements, first lumen 96 may be configured for "rapid exchange" (RE) delivery, in other arrangements, a separate guidewire lumen may be used.

A second lumen 100 may extend from a proximal end of sheath 92 to an opening 102. Optionally, an additional device may be advanced through second lumen 100 and into OA 4. For example, a guidewire may be advanced through second lumen 100, out through opening 102, and into OA 4 such that one or more additional devices (e.g., balloons, stents, etc.) may be advanced into OA 4 for one or more additional procedures. A third lumen 104 may extend from a proximal end of sheath 92 to an opening 106, thereby enabling fluid communication between a region of ICA 2 distal of first balloon 94 and a region of ICA 2 proximal of first balloon 94. In such a manner, retrograde blood flow of ICA 2 and/or OA 4 may be passed through opening 106, through third lumen 104, and permitted to pass through a filter (not shown) and venous return line (not shown) so as to introduce the retrograde blood flow into a venous site (e.g., the IJV) via any appropriate manner.

Figure 7A:
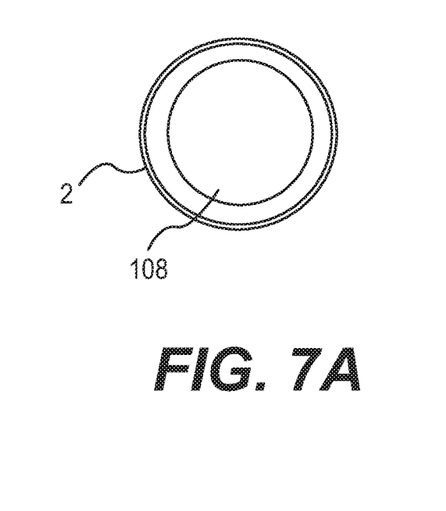
FIGS. 7A and 7B illustrate exemplary cross-sectional shapes of a secondary balloon associated with the system of FIG. 6.
Figure 7B:
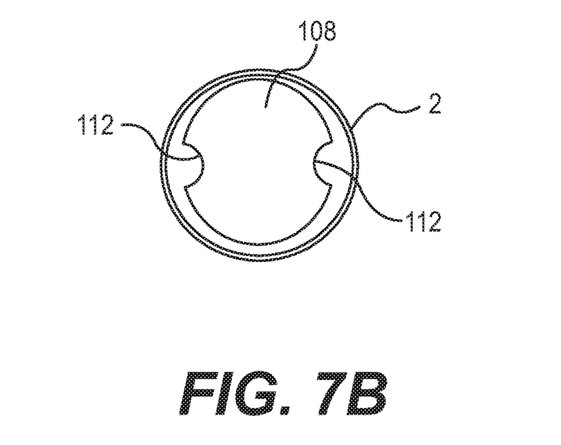

A second balloon 108 positioned on or coupled to a shaft 110. Shaft 110 and second balloon 108 may be delivered distally of first balloon 94 via first lumen 96. A relative positioning between first balloon 94 and second balloon 108 may be adjusted by manipulation (e.g., movement) of one or both of shaft 110 and sheath 92. Second balloon 108 may be a compliant balloon and constructed of any appropriate materials (e.g., urethane polymer or thermoplastic rubber elastomer). Second balloon 108 may have any appropriate shape and size. For example, upon expansion of second balloon 108, a cross-sectional dimension (e.g., diameter) of second balloon 108 may be sized so as to restrict blood flow past second balloon 108. That is, expansion of second balloon 108 may induce a venturi effect so as to increase a blood flow rate, and thereby, induce retrograde blood flow in OA 4, as will be described in further detail. As opposed to first balloon 94, second balloon 108 is not configured to form a complete seal against the wall of ICA 2. Rather, as shown in FIGS. 7A and 7B, balloon 108 may have a cross-sectional shape or size configured to be spaced from a wall of ICA 2. That is, as shown in FIG. 7A, balloon 108 may have a generally circular cross-sectional shape where a diameter of the balloon 108 is smaller than a diameter of ICA 2 so that blood flow may continue to pass between an exterior surface of balloon 108 and an interior wall or surface of ICA 2. In another arrangement, as shown in FIG. 7B, an exterior surface of balloon 108 may include one or more grooves, recesses, or channels 112 to promote blood flow within ICA 2.

Additionally, the shape and/or size of second balloon 108 may be adjustable so as to provide dynamic control of blood flow around or past second balloon 108. That is, following expansion of second balloon 108 to a first size and/or shape, an amount of inflation fluid from a source of inflation fluid (e.g., a gas such as air, or a liquid such as water or saline) to second balloon 108 may be adjusted so as to increase and/or decrease, as desired, a size or shape of second balloon 108.

After accessing ICA 2 via any appropriate manner, the medical professional may position a guidewire within the vasculature of a subject and sheath 92 may be advanced over the guidewire (via first lumen 96) into position within ICA 2, as shown in FIG. 6. That is, sheath 92 may be advanced until first balloon 94 extends into ICA 2, just past the junction between CCA 10 and ICA 2, and distal to the junction between CCA 10 and ECA 8. In such a manner, antegrade blood flow between CCA 10 and ECA 8 is maintained. Once in position, the guidewire may be removed from first lumen 96 of sheath 92.

Next, first balloon 94 may be expanded. That is, source 98, coupled to first lumen 96, may be actuated so as to inflate first balloon 94 and to block antegrade blood flow in ICA 2. First balloon 94 may be expanded so as to contact a wall of ICA 2 upstream of OA 4 and downstream of the junction between CCA 10 and ICA 2. Additionally, shaft 110 may be extended through first lumen 96 so as to advance second balloon 108 to a desired location within ICA 2. As shown in FIG. 6, for example, second balloon 108 may be advanced to a location distal to OA 4. Upon positioning of second balloon 108 within the vasculature, a source of inflation fluid may be delivered to second balloon 108 (e.g., via shaft 110) to inflate or otherwise expand second balloon 108, thereby increasing a blood flow rate of blood in the ICA 2, and inducing retrograde blood flow in OA 4 while maintaining antegrade blood flow in ECA 8. That is, inflation or expansion of one or both of first balloon 94 and second balloon 108 induces a pressure differential in the vasculature such that retrograde blood flow is induced from OA 4 towards ICA 2. The induced retrograde blood flow may be passed through first balloon 94 and through sheath 92 via third lumen 104. As such, any plaque, emboli, or other material dislodged and/or fragmented may be prevented from flowing from ICA 2 toward the eye 6 via OA 4, thereby preventing an embolic event (e.g., blindness, stroke, etc.).

A proximal end of third lumen 104 may be coupled to a filter and a return line (not shown) to return the filtered retrograde blood flow into a venous return site (e.g., into the internal jugular vein (IJV) of the subject) via any appropriate manner. Optionally, an additional device (e.g., one or more of a guidewire, a balloon, a stent, etc.) may be advanced through second lumen 100 and into OA 4 for one or more additional procedures, if deemed necessary or desirable by a medical professional.

In further arrangements, shaft 110 and second balloon 108 may be omitted. In such arrangements, first balloon 94 may be used alone so as to impede antegrade blood flow in ICA 2.

While principles of the present disclosure are described herein with reference to illustrative examples for particular applications, it should be understood that the disclosure is not limited thereto. For example, in any of the above noted arrangements, rather than returning induced retrograde blood flow through a filter and into a venous return site, the blood may be removed via a source of negative pressure (e.g., suction from a syringe) and discarded. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A method, comprising:
inflating a first balloon within an internal carotid artery so as to block antegrade flow of blood into an ophthalmic artery;
maintaining antegrade flow of blood in the internal carotid artery via a perfusion lumen in the first balloon; and
inserting a device into the ophthalmic artery via a lumen extending through a portion of the first balloon to a side opening in the first balloon, wherein the side opening in the first balloon is a radially outward side opening.

2. The method of claim 1, further comprising inflating a second balloon distally of the ophthalmic artery.

3. The method of claim 2, wherein the perfusion lumen extends through the second balloon, and wherein the maintaining antegrade flow of blood in the internal carotid artery includes maintaining antegrade flow of blood in the internal carotid artery via the perfusion lumen extending through the first balloon and the second balloon.

4. The method of claim 1, further including:
inducing retrograde blood flow in the ophthalmic artery of the subject.

5. The method of claim 1, wherein inflating the first balloon forms a seal against a wall of the internal carotid artery.

6. The method of claim 1, further including positioning the first balloon within internal carotid artery over a guidewire via a guidewire lumen.

7. A method, comprising:
inflating a first balloon within an internal carotid artery of a subject proximal of an ophthalmic artery of the subject;
inflating a second balloon within the internal carotid artery distal of the ophthalmic artery;
impeding, via at least one of the inflating the first balloon or the inflating the second balloon, antegrade blood flow in the ophthalmic artery;
maintaining antegrade blood flow in the internal carotid artery of the subject via a perfusion lumen; and
inserting a device into the ophthalmic artery via a lumen extending through a portion of the first balloon to a side opening in the first balloon.

8. The method of claim 7, further including:
inducing retrograde blood flow in the ophthalmic artery.

9. The method of claim 8, further including:
passing the induced retrograde blood flow through a channel of the first balloon.

10. The method of claim 7, wherein the passing the induced retrograde blood flow through the channel of the first balloon includes imparting negative pressure to the channel of the first balloon.

11. The method of claim 7, further including distally advancing the second balloon relative to the first balloon via a shaft.

12. The method of claim 7, further including adjusting a degree of expansion of the second balloon to increase a blood flow rate in the internal carotid artery.

13. The method of claim 7, wherein the inflating the second balloon does not form a complete seal against a wall of the internal carotid artery.

14. A method, comprising:
positioning a balloon within an internal carotid artery, the balloon including an opening extending through a sidewall of the balloon, wherein the sidewall of the balloon is a radially outward sidewall of the balloon;
expanding the balloon so as to contact a wall of the internal carotid artery; and
aligning the opening of the balloon with an ophthalmic artery;
wherein the expanding the balloon includes adjusting a blood flow rate of the ophthalmic artery.

15. The method of claim 14, further including permitting blood flow through the opening of the balloon.

16. The method of claim 15, wherein permitting blood flow through the opening includes permitting induced retrograde blood from the ophthalmic artery, through the opening, to a location proximal of the balloon.

17. The method of claim 14, further including fluidly coupling a region of the internal carotid artery proximal of the balloon with a region of the internal carotid artery distal of the balloon via a lumen disparate from the sidewall opening of the balloon.

* * * * *

UNITED STATES PATENT AND TRADEMARK OFFICE
CERTIFICATE OF CORRECTION

PATENT NO. : 10,398,880 B2
APPLICATION NO. : 16/178163
DATED : September 3, 2019
INVENTOR(S) : Robert Vidlund and Michael Calhoun It is certified that error appears in the above-identified patent and that said Letters Patent is hereby corrected as shown below:

In the Claims

In Line 1 of Claim 10, "The method of claim 7", should read as "The method of claim 9".

Signed and Sealed this
Seventeenth Day of March, 2020

Andrei Iancu
*Director of the United States Patent and Trademark Office*